(12) United States Patent
Coope et al.

(10) Patent No.: US 9,068,209 B2
(45) Date of Patent: Jun. 30, 2015

(54) GENE SYNTHESIS BY CONVERGENT ASSEMBLY OF OLIGONUCLEOTIDE SUBSETS

(75) Inventors: Robin Coope, Vancouver (CA); Daniel Horspool, Montreal (CA); Robert A. Holt, North Vancouver (CA)

(73) Assignee: British Columbia Cancer Agency Branch, Vancouver (CA)

( * ) Notice: Subject to any disclaimer, the term of this patent is extended or adjusted under 35 U.S.C. 154(b) by 1228 days.

(21) Appl. No.: 12/991,694

(22) PCT Filed: May 12, 2009

(86) PCT No.: PCT/IB2009/051958
§ 371 (c)(1),
(2), (4) Date: Jan. 1, 2011

(87) PCT Pub. No.: WO2009/138954
PCT Pub. Date: Nov. 19, 2009

(65) Prior Publication Data
US 2011/0287490 A1    Nov. 24, 2011

Related U.S. Application Data

(60) Provisional application No. 61/071,710, filed on May 14, 2008.

(51) Int. Cl.
| C12P 19/34 | (2006.01) |
| C07H 21/00 | (2006.01) |
| C12Q 1/68  | (2006.01) |
| C12N 15/10 | (2006.01) |
| C12N 15/66 | (2006.01) |

(52) U.S. Cl.
CPC ............ *C12P 19/34* (2013.01); *C07H 21/00* (2013.01); *C12Q 1/6846* (2013.01); *C12N 15/10* (2013.01); *C12N 15/66* (2013.01)

(58) Field of Classification Search
USPC ............................................. 435/91.1, 91.2
See application file for complete search history.

(56) References Cited

U.S. PATENT DOCUMENTS

| 5,114,839 A |    | 5/1992  | Blocker |            |
|-------------|----|---------|---------|------------|
| 5,763,227 A |    | 6/1998  | Blocker |            |
| 5,879,907 A | *  | 3/1999  | Aberg et al. | 435/69.1 |
| 5,888,737 A |    | 3/1999  | DuBridge | 435/6    |
| 5,935,527 A |    | 8/1999  | Andrus  | 422/131    |
| 5,942,609 A |    | 8/1999  | Hunkapiller | 536/25.3 |
| 6,083,726 A |    | 7/2000  | Mills   | 435/91.1   |
| 6,479,262 B1 |   | 11/2002 | Delagrave | 435/91.1 |
| 6,521,427 B1 |   | 2/2003  | Evans   | 425/91.1   |
| 6,670,127 B2 |   | 12/2003 | Evans   | 435/6      |
| 7,183,406 B2 |   | 2/2007  | Belshaw | 536/25.3   |
| 7,208,295 B2 |   | 4/2007  | Faham   | 435/91.1   |
| 7,323,320 B2 |   | 1/2008  | Oleinikov | 435/91.5 |
| 7,544,793 B2 |   | 6/2009  | Guo     | 536/25.3   |
| 7,563,600 B2 |   | 7/2009  | Oleinikov | 435/91.1 |
| 2003/0228602 A1 | * | 12/2003 | Parker et al. | 435/6 |
| 2006/0194214 A1 | * | 8/2006 | Church et al. | 435/6 |
| 2007/0004041 A1 |   | 1/2007 | Church | 435/455 |
| 2007/0054277 A1 |   | 3/2007 | Evans | 435/6 |
| 2007/0269870 A1 |   | 11/2007 | Church | 435/91.2 |
| 2009/0035823 A1 |   | 2/2009 | Soldatov | 435/91.2 |
| 2009/0087840 A1 |   | 4/2009 | Baynes | 435/6 |

FOREIGN PATENT DOCUMENTS

WO          WO 90/00626          1/1990

OTHER PUBLICATIONS

Chen et al., Scand. J. Immunol. 35, 539-549 (1992).*
Borodina et al, "Ligation-based synthesis of oligonucleotides with block structure," Analytical Biochemistry, 318: 309-313 (2003).
Hoover et al, "DNAWorks: an automated method for designing oligonucleotides for PCR-based gene synthesis," Nucleic Acids Research, 30(10): e43 (2002).
International application PCT/IB2009/051958 Search Report, (2009).
International application PCT/IB2009/051958 Written Opinion, (2009).
Larsen et al, "Computationally optimized DNA assembly of synthetic genes," Int. J. Bioinform. Res. Appl., 4(3): 324-336 (2008).
Lededenko et al, "Method of artificial DNA splicing by direct ligation (SDL)," Nucleic Acids Research, 19(24): 6757-6761 (1991).
Linshiz et al, "Recursive construction of perfect DNA molecules from imperfect oligonucleotides," Molecular Systems Biology, 4: 191 (2008).
Narang et al, "'In vitro' method of assembling a synthetic gene," Biochem. Biophys. Res. Comm., 134 (1): 407-411 (1986).
Richmond et al, "Amplification and assembly of chip-eluted DNA (AACED): a method for high-throughput gene synthesis," Nucleic Acids Research 32(17): 5011-5018 (2004).
Rubin et al, "Convergent DNA synthesis: a non-enzymatic dimerization approach to circular oligodeoxynucleotides," Nucleic Acids Research, 23(17): 3547-3553 (1995).
Xiong et al, "Chemical gene synthesis: strategies, softwares, error corrections, and applications," FEMS Microbiol. Rev., 32: 522-540 (2008).
Xu et al, "High sequence fidelity in a non-enzymatic DNA autoligation reaction," Nucleic Acids Research, 27(3): 875-881 (1999).

(Continued)

*Primary Examiner* — Kenneth Horlick
(74) *Attorney, Agent, or Firm* — Stephen C. Macevicz

(57) ABSTRACT

The invention provides a system and method for synthesizing polynucleotides by solid phase assembly oligonucleotide precursors, in accordance with the method, a polynucleotide is partitioned into an ordered set of subunits, wherein each subunit is assembled in a single reaction from a subset of oligonucleotide precursors that uniquely anneal together to produce the subunit. The subunits are then assembled to form the desired polynucleotide. An important feature of the invention is the selection of subunits that are free of undesired sequence elements, such as palindromes, repetitive sequences, and the like, which would result in more than one subunit product alter ligating a pool of oligonucleotide precursors.

18 Claims, 6 Drawing Sheets

(56) References Cited

OTHER PUBLICATIONS

Young et al, "Two-step total gene synthesis method," Nucleic Acids Research, 32(7): e59 (2004).
Zhou et al, "Microfluidic PicoArray synthesis of oligodeoxynucleotides and simultaneous assembling of multiple DNA sequences," Nucleic Acids Research, 32(18): 5409-5417 (2004).
Kaczorowski et al, "Genomic DNA sequencing by SPEL-6 primer walking using hexamer ligation," Gene, 223: 83-91 (1998).
Kieleczawa et al, "DNA sequencing by primer walking with strings of contiguous hexamers," Science, 258: 1787-1791 (1992).
Szybalski, "Proposal for sequencing DNA using ligation of hexamers to generate sequential elongation primers (SPEL-6)," Gene, 90: 177-178 (1990).

* cited by examiner

```
                        SEQUENCE LISTING

<160> NUMBER OF SEQ ID NOS: 9

<210> SEQ ID NO 1
<211> LENGTH: 40
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(6)
<223> OTHER INFORMATION: n is a, c, g, or t
<220> FEATURE:
<221> NAME/KEY: misc_feature
<222> LOCATION: (39)..(40)
<223> OTHER INFORMATION: n is a, c, g, or t

<400> SEQUENCE: 1
nnnnnnaccg atcgtaaggc ggccgcctat gcagtcatnn                              40

<210> SEQ ID NO 2
<211> LENGTH: 21
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 2
nnnnaacacg aacgtccann n                                                  21

<210> SEQ ID NO 3
<211> LENGTH: 42
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (1)..(4)
```

```
<223> OTHER INFORMATION: n is a, c, g, or t
<220> FEATURE:
<221> NAME/KEY: misc_feature
<222> LOCATION: (40)..(42)
<223> OTHER INFORMATION: n is a, c, g, or t

<400> SEQUENCE: 3
nnnnaactcg aaacacacac acacacacac gaacgtccan nn                              42

<210> SEQ ID NO 4
<211> LENGTH: 24
<212> TYPE: DNA
<213> ORGANISM: Unknown
<220> FEATURE:
<223> OTHER INFORMATION: Probe
<220> FEATURE:
<221> NAME/KEY: misc_feature
<222> LOCATION: (10)..(24)
<223> OTHER INFORMATION: n is a, c, g, or t

<400> SEQUENCE: 4
ggaagactgn nnnnnnnnnn nnnn                                                  24

<210> SEQ ID NO 5
<211> LENGTH: 31
<212> TYPE: DNA
<213> ORGANISM: Unknown
<220> FEATURE:
<223> OTHER INFORMATION: Probe

<400> SEQUENCE: 5
cttccaagct tccttccttc catatgctca c                                          31

<210> SEQ ID NO 6
<211> LENGTH: 32
<212> TYPE: DNA
<213> ORGANISM: Homo sapiens

<400> SEQUENCE: 6
gtgggcatgg gtcagaagga ttcctatgtg gg                                         32

<210> SEQ ID NO 7
<211> LENGTH: 32
<212> TYPE: DNA
<213> ORGANISM: Homo sapiens

<400> SEQUENCE: 7
cgacgaggcc cagagcaaga gaggcatcct ca                                         32

<210> SEQ ID NO 8
<211> LENGTH: 32
<212> TYPE: DNA
<213> ORGANISM: Homo sapiens

<400> SEQUENCE: 8
ccctgaagta ccccatcgag cacggcatcg tc                                         32

<210> SEQ ID NO 9
<211> LENGTH: 32
<212> TYPE: DNA
<213> ORGANISM: Homo sapiens

<400> SEQUENCE: 9
accaactggg acgacatgga gaaatctgg ca                                          32
```

GENE SYNTHESIS BY CONVERGENT ASSEMBLY OF OLIGONUCLEOTIDE SUBSETS

This application is a continuation of International Application No. PCT/IB2009/051958, filed May 12, 2009, which claim benefit of U.S. Provisional Application No. 61/071,710 filed May 14, 2008, which applications are incorporated herein by reference in their entireties.

FIELD OF THE INVENTION

The invention relates generally to systems and methods for synthesizing polynucleotides, and more particularly, to systems and methods for synthesizing genes by assembly and ligation of subsets oligonucleotide precursors.

BACKGROUND

Many biotechnological applications require the use and manipulation of gene-sized polynucleotide fragments, including applications in metagenomics, metabolic engineering, and genetic analysis. Metagenomic studies have revealed a wealth of genes encoding novel biochemical pathways and biocatalysts that potentially could play important roles in industrial processes, such as the extraction of fuels from refractory petroleum deposits, the conversion of agricultural raw materials into bulk and specialty chemicals, the generation of fuels from renewable resources, the discovery and development of therapeutically useful products, and the like, e.g. Lorenz et al, Nature Reviews Microbiology, 3: 510-516 (2005); Handelsman, Microbiol. Mol. Biol. Rev., 68: 669-685 (2004); Van Hamme et al, Microbiol. Mol. Biol. Rev., 67: 503-549 (2003). It is expected that genes and genetic pathways discovered in metagenomics studies will provide an important source of raw materials for metabolic engineering, that is, the improvement of cellular activities by manipulation of enzymatic, transport, and regulatory functions of cells with the use of recombinant DNA technology, Bailey, Science, 252: 1668-1674 (1991); Lee et al, Curr. Opin. Biotech., 19: 556-563 (2008). In the field of genetic analysis, "padlock" probes and other large circular DNA probes provide effective detection of genetic variation and an approach to reducing genome complexity which could make personal genome sequencing feasible, e.g. Borodina et al, Anal. Biochem. 318: 309-313 (2003); Hardenbol et al, Nature Biotechnology, 21: 673-678 (2003); Nilsson et al, Nature Genetics, 16: 252-255 (1997); Porreca et al, Nature Methods, 4: 931-936 (2007); Turner et al, Nature Methods, 6: 315-316 (2009); Dahl et al, Nucleic Acids Research, 33: e71 (2005). However, all of these applications in metabolic engineering and genetic analysis depend on the availability of gene-sized DNA fragments that can be synthesized conveniently and inexpensively.

Phosphoramidite-based solid phase DNA synthesis has been a crucial technique for many, if not all, biotechnology applications involving nucleic acid manipulations. However, despite huge gains in efficiency over the years, its practical application is limited to the direct synthesis of polynucleotides having at most 100 to 200 bases, e.g. Hecker et al, Biotechniques, 24: 256-260 (1998). Because of this, many convergent or hierarchical synthesis approaches have been developed for assembling gene-sized fragments of DNA, i.e. fragments in the range of from one to several hundred bases to several thousand bases. In such approaches, sets of pre-synthesized pre-purified oligonucleotides specific for a desired sequence are custom synthesized and assembled into a gene-sized fragment using a variety of enzymatic techniques, e.g. Czar et al, Trends in Biotechnology, 27: 63-72 (2009); Tian et al, Nature, 432: 1050-1054 (2004); Xiong et al, FEMS Microbiol. Rev., 32: 522-540 (2008); Chen et al, J. Am. Chem. Soc., 116: 8799-8800 (1994). Unfortunately, none of these approaches provide a general solution to the increasing demand for inexpensive and conveniently manufactured gene-sized polynucleotides for applications in genetic engineering and analysis.

In view of the above, it would be useful to have available a technique for routine non-custom synthesis of large polynucleotide fragments for use in metabolic engineering and genetic analysis.

SUMMARY OF THE INVENTION

The invention provides a system and method for synthesizing polynucleotides by solid phase assembly oligonucleotide precursors. In accordance with the method, a polynucleotide is partitioned into an ordered set of subunits, wherein each subunit is assembled in a single reaction from a subset of oligonucleotide precursors that uniquely anneal together to produce the subunit. The subunits are assembled to form the desired polynucleotide. An important feature of the invention is the use of oligonucleotide precursors selected from completes sets of oligonucleotides of every sequence of a given length, e.g. 6-mers, 7-mers, 8-mers, or the like, thereby permitting routine polynucleotide assembly. Another important feature of the invention is the selection of subunits (referred to herein as "palindromeless subunits") that are free of sequence elements, such as palindromes and repetitive sequences, which would result in more than one subunit product after a subset of oligonucleotides was annealed and ligated together or which would form other undesired side products, such as repetitive solution phase ligation products.

In one aspect, the invention includes a method of synthesizing a polynucleotide on a solid support from a set of oligonucleotide precursors comprising the following steps: (a) partitioning the polynucleotide into an ordered set of palindromeless subunits with respect to a set of oligonucleotide precursors, each palindromeless subunit comprising a subset of oligonucleotide precursors capable of annealing together to form a unique duplex; and (b) successively ligating the oligonucleotide precursors of each subset to an initializing duplex with a complementary end, the initializing duplex being attached to a solid support, and each subset being ligated in an order corresponding to the ordered set of palindromeless subunits to form the polynucleotide. Preferably, the palindromeless subunits are releasably attached or connected to the initializing duplexes, so that they can readily be released and separated for use in subsequent reactions.

In another aspect, the invention includes a method of synthesizing a polynucleotide from a set of oligonucleotide precursors comprising the steps of (a) determining for the polynucleotide an ordered set of palindromeless subunits with respect to a set of oligonucleotide precursors, each palindromeless subunit overlapping adjacent palindromeless subunits of the ordered set, the ordered set including terminal subunits each having a primer binding site releasably attached thereto, and each palindromeless subunit comprising a subset of oligonucleotide precursors capable of annealing together to form a unique duplex; (b) synthesizing each palindromeless subunit of the ordered set on a separate solid support by ligating a subset of oligonucleotide precursors to a complementary end of an initializing duplex attached the solid support; and (c) combining in a polymerase chain reaction the palindromeless subunits from the solid supports and primers specific for the primer binding sites of the terminal subunits so that the palindromeless subunits and primers undergo successive cycles of denaturation and polymerase extension until the polynucleotide is formed.

In still another aspect, the invention provides a method of synthesizing a polynucleotide from a set of oligonucleotide precursors comprising the steps of: (a) partitioning a polynucleotide into an ordered set of palindromeless subunits with respect to a set of oligonucleotide precursors, each palindromeless subunit comprising a subset of oligonucleotide precursors capable of annealing together to form a unique duplex; (b) ligating the oligonucleotide precursors of each subset to an initializing duplex with a complementary end to form a palindromeless subunit that is releasably attached to a solid support; (c) repeating step (b) until the ordered set of palindromeless subunits is synthesized; and (d) ligating the ordered set of palindromeless subunits together to form the polynucleotide.

In another aspect, the invention provides a method of synthesizing a polynucleotide from a subset of oligonucleotide precursors comprising the steps of: (a) providing a plurality of oligonucleotides capable of annealing to one another to form a polynucleotide having non-ligatable nicks; and (b) combining in a reaction mixture the plurality of oligonucleotides under annealing conditions such that a kinase activity is present for attaching 5'-phosphates to the oligonucleotides so that ligatable nicks are formed and such that a ligase activity is present for ligating ligatable nicks to form phosphodiester bonds between oligonucleotides, thereby forming the polynucleotide. Preferably, in this aspect, the kinase activity is provided by T4 polynucleotide kinase and the ligase activity is provided by T4 DNA ligase.

In another aspect, the invention provides a system for synthesizing a polynucleotide on a solid support from a set of oligonucleotide precursors, the system comprising: (a) a source of oligonucleotide precursors, the source capable of providing a set of oligonucleotide precursors of every sequence of a predetermined length; (b) a partition of a polynucleotide into an ordered set of palindromeless subunits with respect to the set of oligonucleotide precursors, each palindromeless subunit comprising a subset of oligonucleotide precursors capable of annealing together to form a unique duplex; and (c) a solid support in a reaction vessel, the solid support having an initializing duplex or an extended duplex releasably attached thereto, each having an overhang, and the reaction vessel capable of repeated cycles of ligation wherein the oligonucleotide precursors of each subset is combined in the reaction vessel under annealing conditions in an order of the ordered set of palindromeless subunits to form a reaction duplex having a complementary overhang to that of the initializing duplex or the extended duplex attached to the solid support, such that upon ligation a new extended duplex is formed in each cycle, and wherein the polynucleotide is formed on the solid support after each subset of oligonucleotide precursors has been ligated to either the initializing duplex or an extended duplex.

In another aspect, the system of the invention comprises: (a) a source of oligonucleotide precursors, the source capable of providing a set of oligonucleotide precursors of every sequence of a predetermined length; (b) an ordered set of palindromeless subunits with respect to the set of oligonucleotide precursors, the ordered set of palindromeless subunits covering the polynucleotide, each palindromeless subunit overlapping adjacent palindromeless subunits of the ordered set, the ordered set including terminal subunits each having a primer binding site releasably attached thereto, and each palindromeless subunit comprising a subset of oligonucleotide precursors capable of annealing together to form a unique duplex; (c) a plurality of reaction vessels for synthesizing each palindromeless subunit of the ordered set on a separate solid support by ligating a subset of oligonucleotide precursors to a complementary end of an initializing duplex attached the solid support; and (d) a second reaction vessel for combining in a polymerase chain reaction the palindromeless subunits from the solid supports and primers specific for the primer binding sites of the terminal subunits so that the palindromeless subunits and primers undergo successive cycles of denaturation and polymerase extension until the polynucleotide is formed.

The present invention advantageously addresses short comings of present technology by providing a system and methods for routine non-custom synthesis of gene-sized polynucleotides by assembly from sets of short predetermined oligonucleotide precursors. Implementation of the method does not require pre-synthesis of oligonucleotides derived from a target polynucleotide for assembly.

DETAILED DESCRIPTION OF THE INVENTION

Figure 1A:
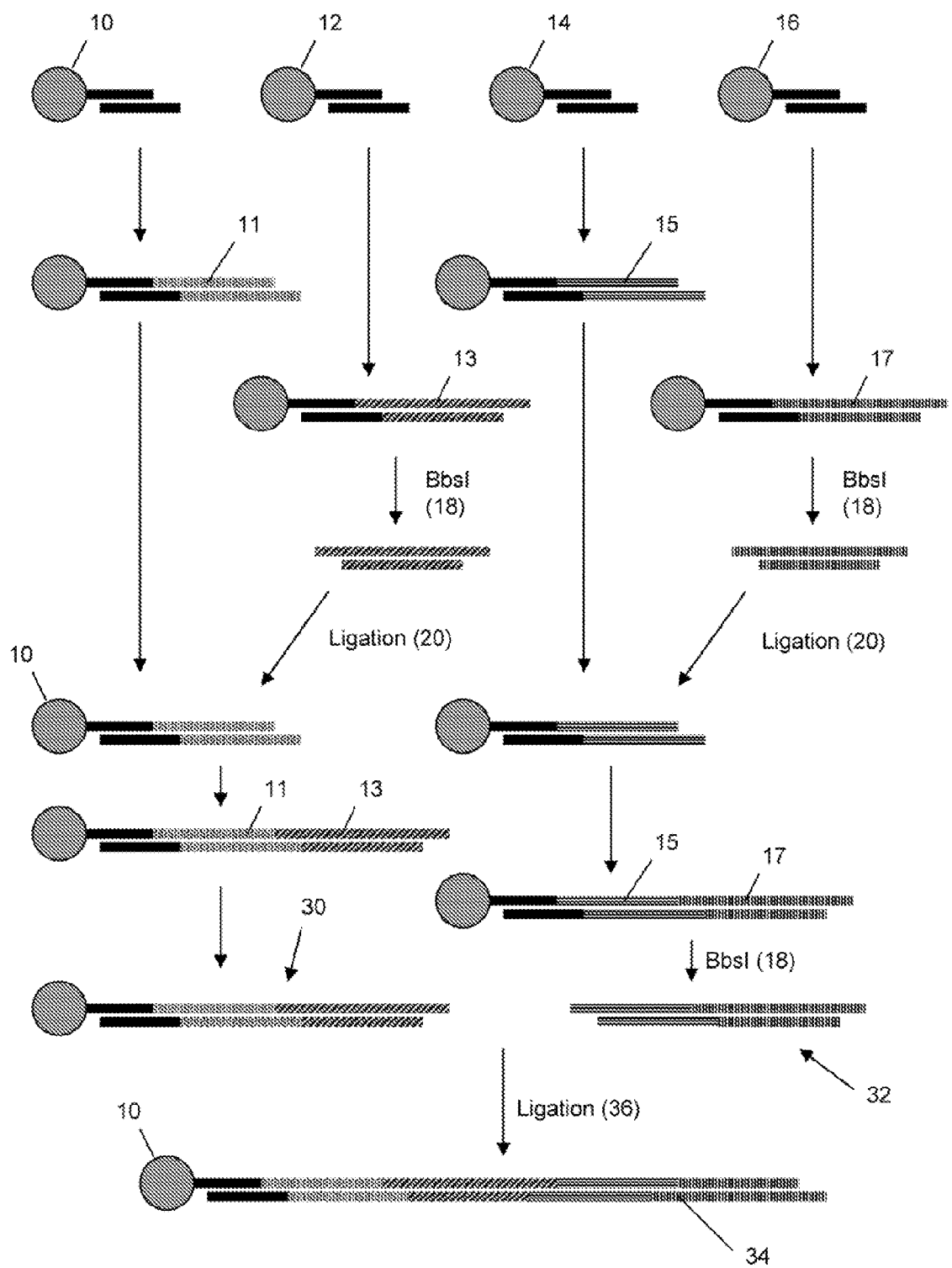
FIG. 1A-1B illustrate preferred schemes for assembling multiple palindromeless subunits into a target polynucleotide.

The practice of the present invention may employ, unless otherwise indicated, conventional techniques and descriptions of organic chemistry, molecular biology (including recombinant techniques), cell biology, biochemistry, and immunology, which are within the skill of the art. Such conventional techniques include, but are not limited to, vector construction, microbial host transformation, selection and application of genetic markers, manipulation of large polynucleotide fragments, preparation of synthetic polynucleotides, application of recombination systems, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al, (2002) *Biochemistry*, $5^{th}$ Ed., W. H. Freeman Pub., New York, N. Y. Casali et al, editors, *E. Coli* Plasmid Vectors: Methods and Applications (Humana Press, Totowa, N.J., 2003).

In one aspect, the invention is a system and method for convergent or hierarchical synthesis of a desired polynucleotide from a set of oligonucleotide precursors. The desired polynucleotide is assembled from palindromeless subunits comprising subsets of oligonucleotide precursors. Such assembly may take place in a variety of ways including, but not limited to the following: (i) in one reaction after separate assembly and ligation of each palindromeless subunit, where such assembly takes place by ligating the subunits together, (ii) in a series of reactions where all subunits except one is released from its solid support, after which each release subunit is ligated in separate reactions to the unreleased subunit, (iii) in a series of pairwise reactions in which two subunits are ligated at a time, after which products of those reactions are ligated pairwise, and so on, until the polynucleotide is obtained, (iv) in a series of reactions wherein an initializing duplex attached to a solid support is progressively extended by successively ligating each subset of oligonucleotide precursors in the same order as the ordering of the palindromeless subunits in the polynucleotide, (v) in a polymerase chain reaction where overlapping palindromeless subunits are assembled by repeated cycles of denaturation and polymerase extension. Generally, when either oligonucleotide precursors or subunits or higher order fragments are assembled on a solid support in cyclical reactions, the support and attached reaction products preferably undergo wash steps within the cycles. Such wash steps are preferably carried out under non-denaturing conditions so that desired double stranded products are not denatured and lost. The stringency of the non-denaturing wash conditions may be varied according to the nature of the product attached to the solid phase. For example, longer double stranded products may be washed under higher stringency conditions.

In one preferred embodiment, the assembly approach (iii) is employed as illustrated in FIG. 1A, where four subunits (11, 13, 15, and 17) are assembled on separate solid supports (10, 12, 14, and 16, respectively), after which two of the subunits (13 and 17) are cleaved (18) and ligated pairwise (20) to the two subunits (11 and 15) that remain attached to their synthesis supports (10 and 14), referred to herein generally as "intermediate ligation products" or when consisting of two subunits, a "subunit pair." A skilled practitioner would recognize that more than four subunit may readily be prepared for synthesizing longer target polynucleotides. After ligation, subunit pair (15, 17) is cleaved from support (14) and ligated to the end of subunit pair (11, 13) that remains attached to support (10), thereby form a final ligation product (34).

Figure 1B:
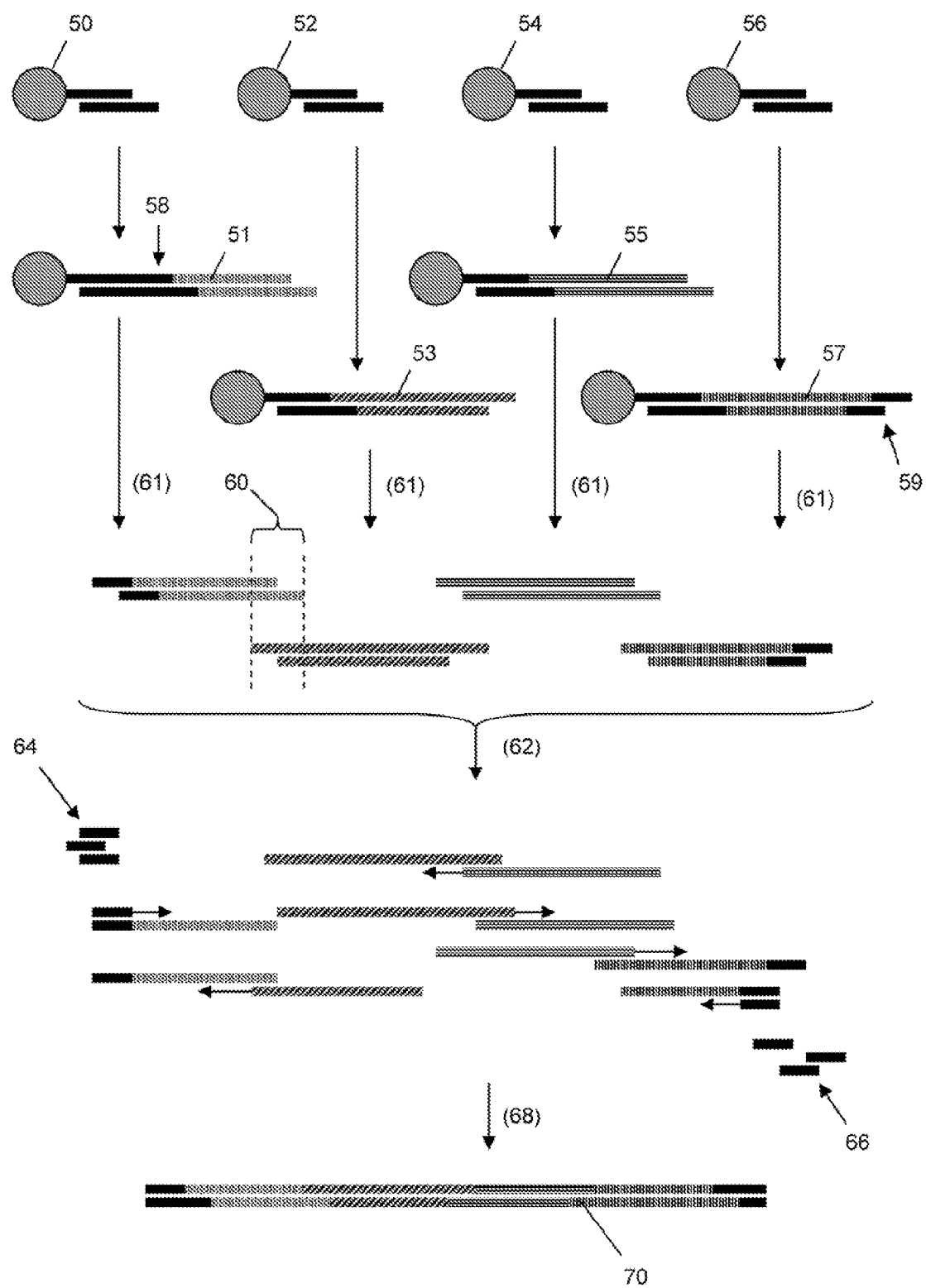

In another preferred embodiment, the assembly approach (v) (via PCR) may be employed as illustrated in FIG. 1B. As in the above example, four palindromeless subunits (51, 53, 55, and 57) are assembled on separate solid supports (50, 52, 54, and 56, respectively). Terminal subunits (51 and 57) additionally contain primer binding sites (58 and 59, respectively), which for terminal subunit (51) may be assembled from oligonucleotide precursors or be introduced as part of the initializing duplex. In this embodiment, subunits (51, 53, 55, and 57) overlap so that in cycles of denaturation, annealing and polymerase extension (68) the ends of adjacent subunit are capable of annealing to one another and serving as primers for extension. In one aspect, such overlaps are in the range of from 16 to 24 basepairs, and preferably, in the range of from 18 to 20 basepairs. After subunits are cleaved (61) from their supports, they are combined (62) with forward and reverse primers (64 and 66, respectively) in a polymerase chain reaction (68) in which target polynucleotide (70) is produced as the final extension product. Primer binding sites (58 and 59) may be engineered to contain type IIs restriction endonuclease sites so that after PCR (68) a target polynucleotide with desired ends is produced. Applicants intend that this aspect of their invention includes the use of palindromeless subunits in any of the many different versions of PCR-based gene synthesis, including, but not limited to single- and two-step assembly, thermodynamically balanced inside-out, and others, e.g. reviewed by Xiong et al, FEMS Microbiol. Rev. 32: 522-540 (2008), and further disclosed in the following references, which are incorporated by reference: Chen et al, J. Am. Chem. Soc., 116: 8799-8800 (1994); Evans, U.S. Pat. No. 6,670,127; Stemmer et al, Gene, 49-53 (1995); and the like.

Figure 1C:
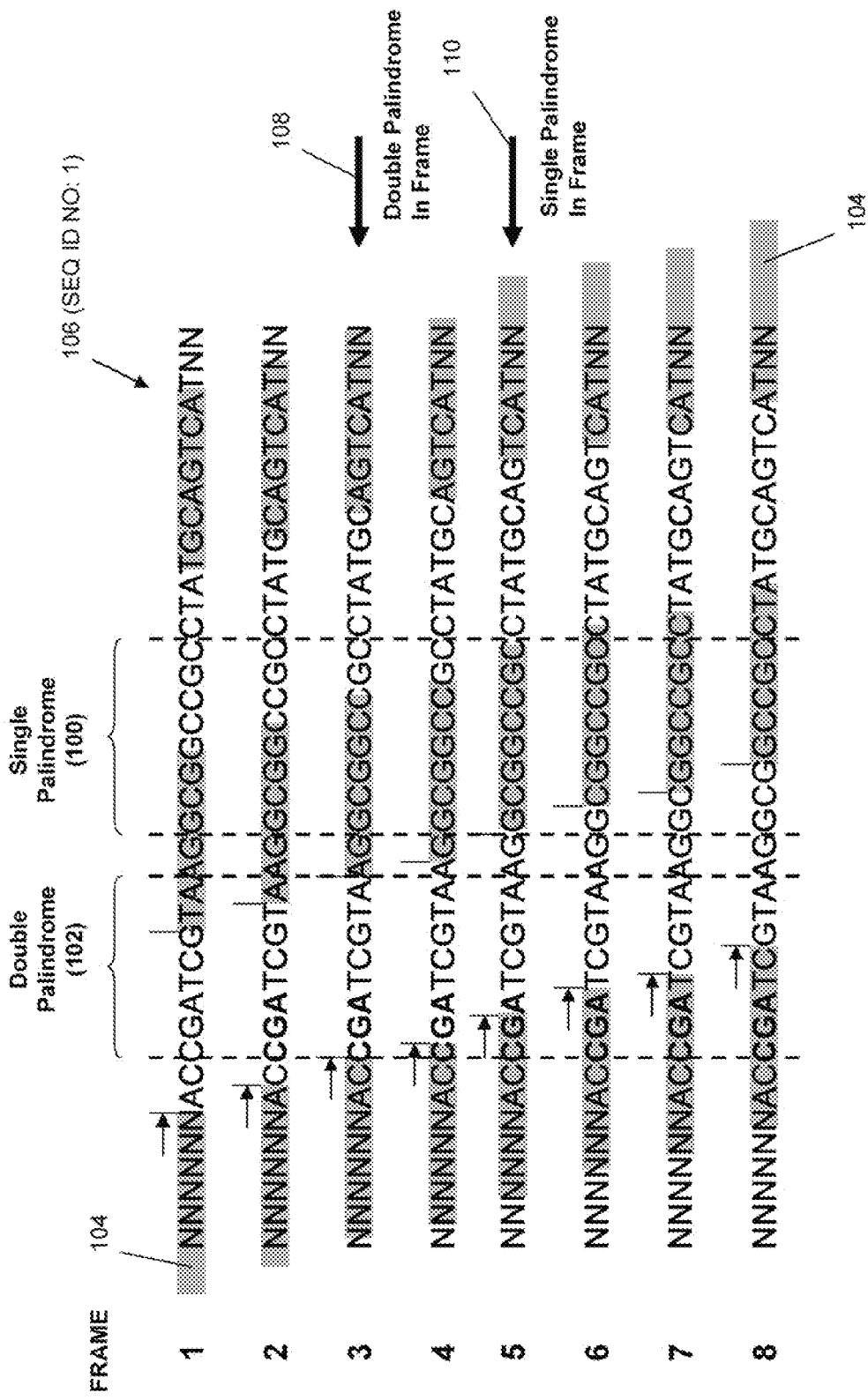
FIG. 1C illustrates types of palindromes and the concept of tiling oligonucleotide precursors for choosing subsets making up a palindromeless subunit.

Oligonucleotide precursors grouped together as a potential subset can contain several undesirable sequence elements that lead to the rejection of the grouping as a subset used in the invention, i.e. a palindromeless subunit. Such undesired sequence elements include, but are not limited to, the following: (a) Palindromes. Palindromic sequences are undesired because they permit oligonucleotides containing them to self-assemble in ligation reactions to form incorrect products. FIG. 1C illustrates two possible types of palindromes that give rise to such problems: a single palindrome (100) making up an entire 8-mer oligonucleotide precursor (GCGGCCGC, a Not I site), and a double palindrome (102) (CGATCGTA), which may form a duplex with two-base overhangs that may permit further undesired concatenations the duplexes. (b) Palindromic Overhangs of Initializing and Extended Duplexes. Palindromic sequences in overhangs of initializing or extended duplexes, e.g. ATAT, AGCT, and the like, can result in self-ligation of such ends on a solid support, thereby effectively capping the duplexes from any further reactions, e.g. Dubridge et al, U.S. Pat. No. 5,888,737. In one aspect of the invention, overhangs with odd numbers of nucleotides are used, e.g. 1, 3, or 5 (since only overhangs of even numbered nucleotides are capable of being palindromic). (c) Non-Unique Overhangs Within A Subset. If multiple subgrouping or oligonucleotide precursors (that can form a duplex) in a subset have the same complementary overhangs, then they may assemble into multiple distinct duplexes. For example, repetitive sequences give rise to this type of undesired assembly.

The invention in part provides a solution to these problems by partitioning a target polynucleotide into palindromeless subunits with respect to the set of oligonucleotide precursors being used. That is, the invention provides a method of generating sets of subunits each consisting of a subset of oligonucleotide precursors that avoid the above problems. Such partitioning depends on the length of the oligonucleotide precursors being used, as well as the overhang lengths of the initializing duplexes, extended duplexes, and duplex-firming oligonucleotide precursors.

Preferably, criteria in addition to those listed above may be used for selecting subsets of oligonucleotide precursors for palindromeless subunits. Such additional criteria include, but are not limited to, the following: (i) minimization of the size of the subset of oligonucleotide precursors employed in any single reaction (for example, to avoid mismatch ligations), (ii) minimizing the difference in annealing temperature of members of a subset of oligonucleotide precursors, (iii) minimizing the difference in annealing temperatures of the overhangs of different subunits, (iv) whether to employ frame-shifting adaptors or bridging adaptors in the synthesis process (discussed more fully below), (v) whether to minimize the degree of cross-hybridization among the hybrid-forming portions of different oligonucleotide precursors that make up a subunit, and the like.

In regard to criterion (i), the number of oligonucleotide precursors in a subset may vary widely and depends on the size of the overhangs employed, with shorter overhangs leading to smaller sized subsets. In one aspect, for four nucleotide overhangs, the size of a subset may be in the range of from 2 to 128; and more preferably, from 2 to 64; and still more preferably, from 2 to 32; and still more preferably, from 2 to 16. For 3-mer overhangs, preferably, size of subsets are in the range of from 2 to 32; or from 2 to 16; or more preferably, from 2 to 8.

In regard to criterion (v), the notion of minimally cross-hybridizing sets of oligonucleotides developed by Sydney Brenner is applicable, e.g. U.S. Pat. No. 5,846,719; Mao et al, International patent application WO 02/097113; Morris et al, U.S. Pat. No. 6,458,530; and the like. The sequences of oligonucleotides of a minimally cross-hybridizing set differ from the sequences of every other member of the same set by at least one nucleotides, and more preferably, by at least two nucleotides. Thus, each member of such a set cannot form a duplex with the complement of any other member with less than one or two mismatches, as the case may be. This concept may be generalized for the present invention by using a more general measure of duplex stability than number of mismatches. For example, members of a minimally cross-hybridizing set may maximize the difference between the duplex stability of a member sequence and its complement and the average of those of the member sequence and the complements of every other member of the set. Preferably, perfectly matched duplexes of oligonucleotide precursors of the same minimally cross-hybridizing set have approximately the same stability, especially as measured by melting temperature.

Figure 2A:
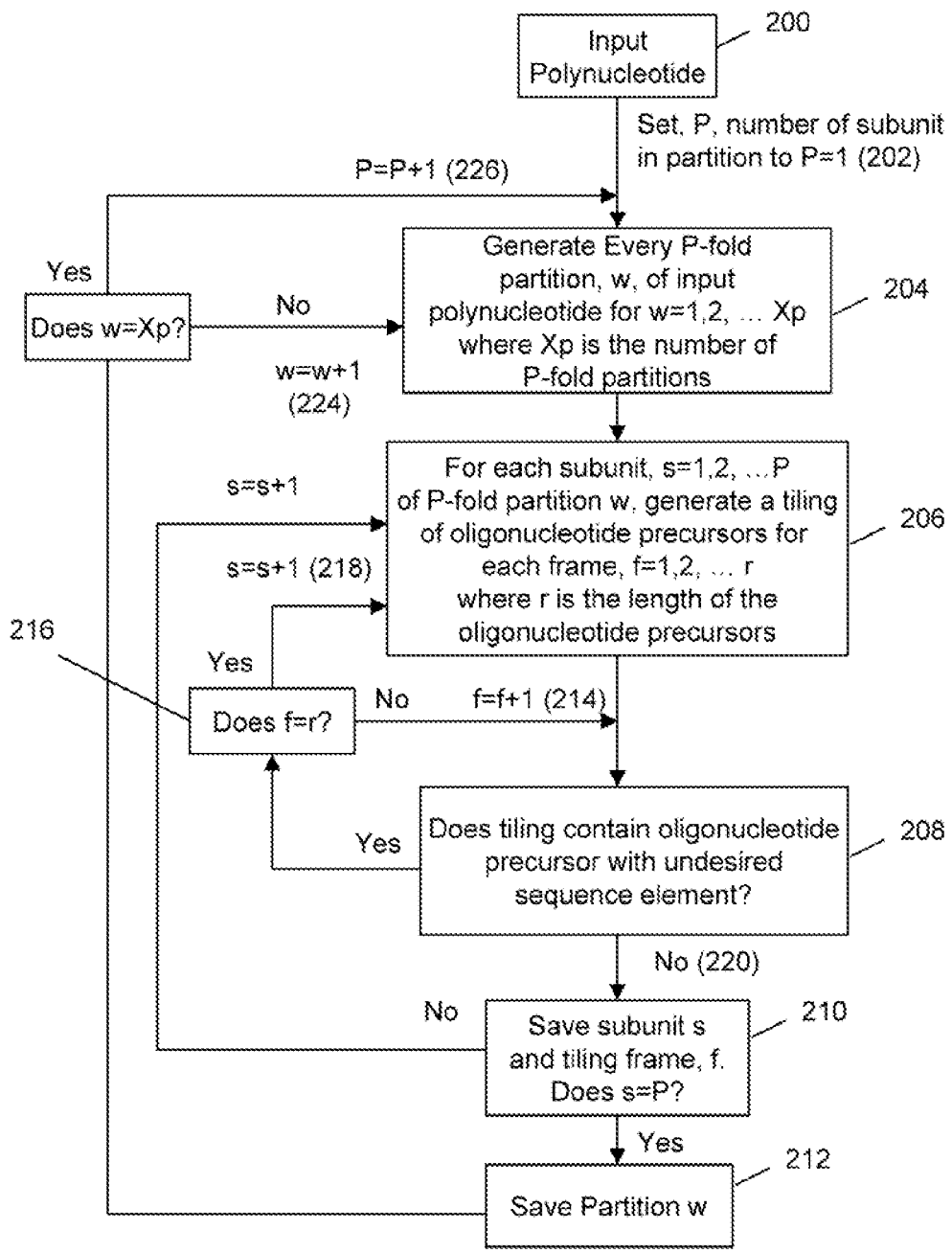
FIG. 2A is a flow chart of a first algorithm for determining oligonucleotide subsets making up palindromeless subunits.

In one aspect the process of partitioning a polynucleotide is illustrated by the flow chart of FIG. 2A. Candidate partitions of input polynucleotide (200) are systematically examined to find the optimal number and locations of subunits (i.e. the optimal partition) to divide it into for synthesis in accordance with the method of the invention. Initially the entire input polynucleotide is take as a single partition, P=1 (202), after which partitions are formed with increasing numbers of candidate subunits until a partition is found that fulfills the oligonucleotide precursor selection constrains discussed above, and in certain preferred embodiments, the additional criteria mentioned above. Every partition, w, of P subunits is generated (204) for a total number Xp, where the subscript "p" is the number of subunits in the partitions. For example, if a target polynucleotide has N nucleotides, then $X_2$=N−1; and $X_3$=(N−1)(N−2); and so on. For each partition, w, every possible tiling of oligonucleotide precursors is examined. An example of such examination is illustrated in FIG. 1C. A tiling of a subunit means a possible reconstruction of the subunit's sequence by an assembly of oligonucleotide precursors in a particular frame. In FIG. 1C, frames are illustrated as alternating gray and white segments (104) that are superimposed on sequence (106) (SEQ ID NO: 1). Different frames (with respect to 8-mer oligonucleotide precursors) of sequence (106) are shown. The number of different frames depends on the length of the oligonucleotide precursors employed. For each frame, every candidate oligonucleotide precursor is checked (206) for undesired sequence elements (and optionally the other criteria mentioned above). If the particular tiling does have an undesired sequence element (208), as would be the case for tiling (or frame) 3 (108) and tiling (frame) 5 (110) in FIG. 1B, then the next tiling is tried (214), unless it is the last tiling (216), in which case the next subunit is examined (218). If no undesired sequence element is detected (220), then the subunit and tiling are saved (210), after which the next subunit is examined (222) or if that was the last subunit of a partition (210), the partition is saved (212) and the next partition is tried (224), unless it is the last partition (226), in which case, the number of subunits in a partition in increased by one and the process is repeated. The process steps may be repeated until all possible partitions are obtained consisting of subunits that are free of undesired sequence elements. The other criteria are then used to select an optimal partition from the candidates. One skilled in the art may use many alternative algorithms or elaborations on the above algorithm for selecting partitions.

Figure 2B:
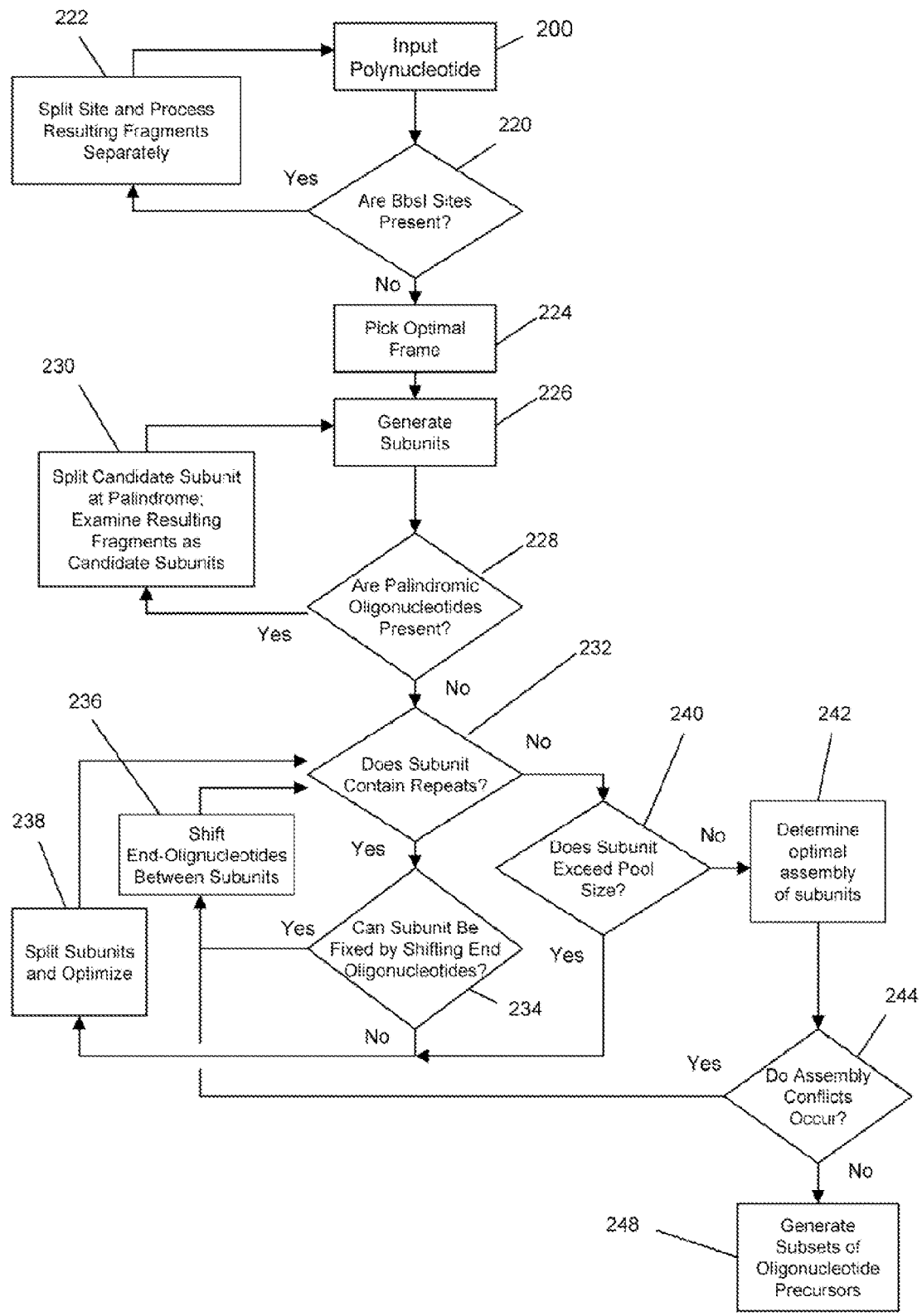
FIG. 2B is a flow chart of a second algorithm for determining oligonucleotide subsets making up palindromeless subunits.

In another aspect of the invention, the process of partitioning a polynucleotide is illustrate by the flow chart of FIG. 2B. The sequence of target polynucleotide (200) is first scanned (220) to determine whether it contains restriction sites identical to that in the initializing duplex for releasing subunits, in this example a BbsI site, but it could be a different site if such were used in the initializing duplex. Alternatively, the loop of scanning for such restriction sites (220) and selecting candidate subunits splitting (222) such sites can be eliminated by releasing subunits without using restriction endonucleases, e.g. by using uracil-DNA glycosylase. Once target polynucleotide (200) is divided into fragments free of such internal restriction sites, an optimal frame for the oligonucleotide precursors is selected (224), i.e. ones with minimal palindromes and repeat sequences within individual oligonucleotide precursors, after which each fragment is divided into candidate subunits (226). Each candidate subunit is scanned for oligonucleotide precursors that encompass palindromes (228), and if a palindrome is present the candidate subunit is split at its site (230) and the process is repeated, otherwise the candidate subunit is scanned for repeat sequences within oligonucleotide precursors (232). If such repeats are detected, the subunit is tested to determine whether shifting the oligonucleotide precursors to an adjacent subunit will remove it as a problem (234), i.e. re-forming adjacent subunits by shifting one or more oligonucleotide precursors from one to the other, then test to determine whether the repeat has been eliminated as a problem (236), after which the process is repeated. If such repeats sequences are not detected, then the number of oligonucleotide precursors in the candidate subunit is determined (240) and if it is above a predetermine value, it is divided (238) and the process is repeated. If the number is acceptable, then it is saved and when all candidate subunits are available, the assembly of subunits is checked to determine whether it results in a unique polynucleotide (242). If the number of oligonucleotide precursors in a candidate subunit exceeds the predetermined value, then the candidate subunit is split (238) and the process is repeated. If no assembly conflicts arise among the candidate subunits (244), then subsets of oligonucleotide precursors are generated for assembling into palindromeless subunits (248), otherwise an attempt to fix the conflicts is made by moving terminal pairs of oligonucleotide precursors between adjacent subunits (236).

Once an ordered set of palindromeless subunits are selected, a solid support with an appropriate initializing duplex is selected. In one referred embodiment, a collection of initializing duplexes are available each of which containing a type IIs restriction site positioned so that its cleavage site corresponds to the end of the target polynucleotide. A broad selection of type IIs restriction endonucleases that may be used with such embodiments are commercially available, for example from New England Biolabs (Beverly, Mass.). Exemplary type IIs restriction endonucleases that may be used with the invention include, but are not limited to, Ear I, Bbs I, Alw I, Bbv I, Bcc I, BceAI, Bfu AI, Bsa I, BsmAI, BsmBI, BspQI, Fok I, Hga I, Mly I, Mme I, Nme AIII, Sap I, Sfa NI, and the like. Also, nicking endonuclease may be used, particularly where a single stranded polynucleotide is desired.

As mentioned above, oligonucleotide precursors comprise a set of oligonucleotides having every possible sequence of a given length. In one aspect of the invention where pre-synthesized oligonucleotide precursors are maintained as separate reagents, sets comprise oligonucleotides of from 4 to 8 nucleotides in length; more preferably, such sets comprise oligonucleotides either six, seven, or eight nucleotides in length. Preferably, oligonucleotide precursors of such sets have a 5' phosphate group for forming a phosphodiester linkage in a ligation reaction. A feature of the invention is the selection of the degree of overlap between oligonucleotide precursors in opposite stands of an assembled subunit; or, equivalently, the selection of overhang length of subunit duplexes. Preferably, for 6-mer oligonucleotide precursors the overhang length is three nucleotides. Preferably, for 7-mer and 8-mer oligonucleotide precursors the overhang length is three or four nucleotides.

preferably, are in the range of from 100 to 5,000 nucleotides or basepairs in length, or still more preferably, are in the range of from 100 to 2000 nucleotides or basepairs in length.

In one aspect of the invention, frame-shifting adaptors may be used in the synthesis process to expand the number of candidate partitions of a target polynucleotide. Such adaptors comprise a duplex containing a type IIs restriction recognition site positioned so that its cleavage site is positioned outside of the adaptor so that when ligated to a duplex (such as a subunit) with a complementary end, it cleaves part of the duplex, thereby shifting the frame of the oligonucleotide precursors in the duplex. An exemplary frame-shifting adaptor for 7-mer or 8-mer oligonucleotides producing subunits with four nucleotide overhangs is as follows (SEQ ID NO: 2).

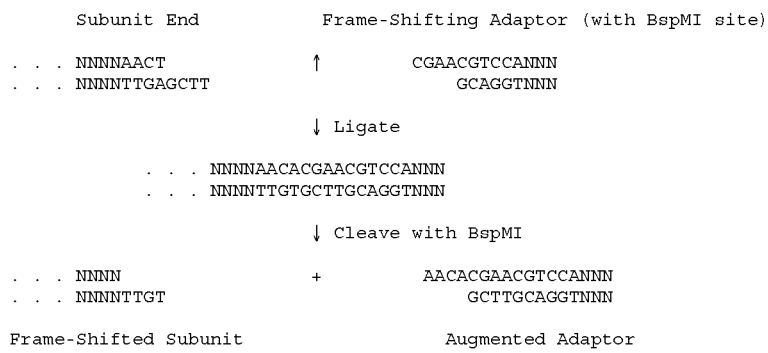

In another aspect of the invention where oligonucleotide precursors are provided by "on-demand" synthesis (discussed more fully below), sets of oligonucleotide precursors comprise oligonucleotide having lengths in the range of from 4 to 14 nucleotides. Moreover, the lengths of oligonucleotide precursors in a given subset may be the same or different; however, the lengths are preferably the same in a given subset. As above, the degree of overlap between oligonucleotide precursors in complementary strands which are also hybrids may vary greatly. Preferably, for 4-mers to 8-mer oligonucleotide precursor, the degree of overlap (and the length of overhangs) is the same as described above. For 9-mer oligonucleotide precursors, preferably the range of overlap is from 5 to 6 nucleotides; for 10-mer oligonucleotide precursors, preferably the range of overlap is from 5 to 7 nucleotides; for 11-mer oligonucleotide precursors, preferably the range of overlap is from 6 to 8 nucleotides; for 12-mer oligonucleotide precursors, preferably the range of overlap is from 6 to 9 nucleotides; for 13-mer oligonucleotide precursors, preferably the range of overlap is from 7 to 10 nucleotides; and for 14-mer oligonucleotide precursors, preferably the range of overlap is from 7 to 11 nucleotides. In one aspect, such sets of oligonucleotide precursor may be used to synthesize gene-sized polynucleotides, which preferably are in the range of from 100 to 10,000 nucleotides or basepairs in length, or more Clearly one of ordinary skill may make many modifications and variants of the above scheme for particular embodiments having different overhangs, different restriction enzymes, and the like. Similarly, bridging adaptors may be used to shift the frame of oligonucleotide precursor tilings by adding nucleotides or to by-pass difficult sequence regions, such as repeat sequences. For example, consider the following segment of a target polynucleotide containing a CA repeat. In one embodiment, such repeat sequence can be ignored by the algorithm for calculating palindromeless subunits. Instead, the repeat may be synthesized separately, as illustrated, then assemble with the palindromeless subunits to give the target polynucleotide (SEQ ID NO: 3).

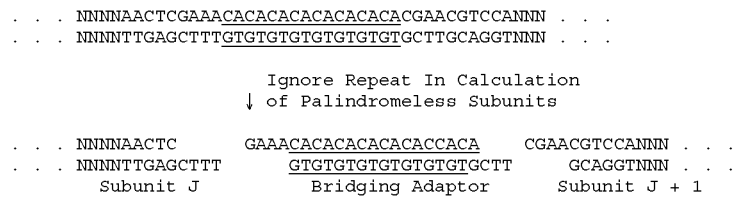

In one embodiment of the present invention, the overlapping sequences are only three bases long i.e. hexamers are combined. In an alternative embodiment of this invention the overlapping sequences would be only two bases i.e. the method could be done with 4mers. In still further embodiments the overlapping sequences are four, five or six bases long i.e. 8-mers, 10-mers or 12-mers are utilized. In still further alternate embodiments combinations of overlapping sequences of varying lengths may be used and any resultant "gaps" may be filled using enzymes to extend the sequence.

In another aspect of the invention, the size of the library may be reduced by grouping together oligonucleotides with no complimentary sequence. In a further aspect of the invention, based on the sequence of the DNA fragment to be assembled, oligonucleotides may be combined into pools with no complimentary sequence in order to reduce the number of assembly steps and manipulations.

Varying the length of intermediate strands in a hierarchical assembly will allow them to be designed in such a way that they have an optimal 3' overhang; different from its neighbors so that when the strands are subsequently combined, misannealing can be avoided. Once approximately double stranded DNAs have been created, they can be cut off the beads with type IIs restriction enzymes and ligated to each other, with annealing directed by their complimentary 3 basepair 3' overhangs.

Once a target polynucleotide is partitioned into an ordered set of palindromeless subunits, the oligonucleotide precursors of each subunit are combined and either ligated together and to an initializing duplex or to an extended duplex, depending on the convergent synthesis scheme being employed. In either case, conventional ligation reaction conditions are employed as described more fully below, after which the solid support(s) with the ligation products are preferably washed to remove unused precursors, ligase if enzymatic ligation is used, and other reactants. After the ligation reaction is complete, the ligation product is released from the solid support, which may be carried out chemically or enzymatically, e.g. by the presence of a restriction site in the initializing duplex. Optionally, incomplete ligation products may be capped in a capping step as described below.

Solid Supports

Oligonucleotides of initializing duplexes may be immobilized on solid supports through any one of a variety or well-known covalent linkages or non-covalent interactions. The support is comprised of insoluble materials, preferably having a rigid or semi-rigid character, and may be any shape, e.g. spherical, as in beads, rectangular, irregular particles, resins, gels, microspheres, or substantially flat. In some embodiments, it may be desirable to create an array of physically separate synthesis regions on the support with, for example, wells, raised regions, dimples, pins, trenches, rods, pins, inner or outer walls of cylinders, and the like.

Preferred solid support materials include agarose, polyacrylamide, magnetic beads (e.g. as disclosed by Stamm et al, pgs. 55-70, in PCR 2: A Practical Approach (IRL Press, Oxford, 1995)), polystyrene (Andrus et al, U.S. Pat. No. 5,262,530), controlled-pore-glass (Caruthers et al, U.S. Pat. No. 4,458,732), polyacrylate, hydroxyethylmethacrylate, polyamide, polyethylene, polyethyleneoxy, or copolymers and grafts of such. Polyethyleneoxy/polystyrene co-polymer is used extensively for small molecule and peptide synthesis and is a particularly preferred solid support of the present invention (Tentagel, Rapp Polymere, Tubingen, Germany). The hydrophilic nature of the polyethyleneoxy groups promotes rapid kinetics and binding when aqueous solvents are used. Other embodiments of solid supports include small particles, membranes, frits, non-porous surfaces, addressable arrays, vectors, plasmids, or polynucleotide-immobilizing media.

Preferably, oligonucleotides are attached by covalent bonds, ionic bonds, or other affinity interactions, to chemically reactive functionality on the solid-supports. Oligonucleotides can be attached to solid-supports at their 3', 5', sugar, or nucleobase sites (e.g. as disclosed by Goodchild, Bioconjugate Chem. 1: 165-187 (1990); Beaucage et al, Tetrahedron, 49: 1925-1963 (1993)). The 3' site for attachment via a linker to the support is preferred due to oligonucleotide synthesis ease and efficiency, and due to the many options available for stable or selectively cleavable linkers (Beaucage et al, Tetrahedron, 48: 2223-2311 (1992)). In this manner, gram to kilogram scale preparations of immobilized oligonucleotides can be obtained at loading ranges of 1-2000 nmoles oligonucleotide per gram of support, and preferably in a range of 500-1000 nmoles oligonucleotide per gram of support.

Immobilization is preferably accomplished by a covalent linkage between the support and the oligonucleotide. The linkage unit, or linker, is designed to be stable and facilitate accessibility of the immobilized nucleic acid to its sequence complement. Alternatively, non-covalent linkages such as between biotin and avidin or streptavidin are useful. A typical method for attaching oligonucleotides is coupling a thiol functionalized polystyrene bead with a 3' thiol-oligonucleotide under mild oxidizing conditions to form a disulfide linker. Examples of other functional group linkers include ester, amide, carbamate, urea, sulfonate, ether, and thioester. A 5' or 3' biotinylated oligonucleotide can be immobilized on avidin or streptavidin bound to a support such as glass or SEPHAROSE™ (Pharmacia Biotech).

Alternatively the 5' terminus of an oligonucleotide can be immobilized to a solid-support. The directionality of the assembled polynucleotide and the component oligonucleotides of the preceding embodiments would thus be reversed, although equally accommodated and efficient.

In alternative embodiments of the present invention, as noted above, the cleavage of oligonucleotide strands from their solid support is not limited to the use of any particular restriction endonuclease or to a restriction enzyme in general. Any enzymatic or chemical process known to those skilled in the art which can cleave DNA strands or chemical linkers that result in the freeing of the support's attached oligonucleotide or duplex can be used. Subsequent chemical or enzymatic reactions may be additionally employed to produce a compatible end for subsequent pairwise or serial ligation reactions.

Oligonucleotide Synthesis

In one aspect of the invention, oligonucleotides for precursors, initializing duplexes, frame-shifting adaptors, and bridging adaptors are conveniently synthesized on automated DNA synthesizers, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

When conventional ligases are employed in the invention, as described more fully below, the 5' end of the probe may be phosphorylated in some embodiments. A 5' monophosphate can be attached to an oligonucleotide either chemically or enzymatically with a kinase, e.g. Sambrook et al, Molecular Cloning: A Laboratory Manual, 2nd Edition (Cold Spring Harbor Laboratory, New York, 1989). Chemical phosphorylation is described by Horn and Urdea, Tetrahedron Lett., 27: 4705 (1986), and reagents for carrying out the disclosed protocols are commercially available, e.g. 5' Phosphate-ON™ from Clontech Laboratories (Palo Alto, Calif.). Preferably, when required, oligonucleotide probes are chemically phosphorylated.

In one aspect of the invention, once palindromeless subunits are determined, oligonucleotide precursors may be synthesized using rapid automated DNA synthesizers optimized for synthesizing short oligonucleotides, e.g. using the dual synthesis-purification method of Andrus et al U.S. Pat. No. 5,935,527. Preferably, a single automated DNA synthesizer is employed which has parallel synthesis capability, e.g. using a plurality of reaction vessels, and which is operationally associated with a control system that specifies the sequences of the oligonucleotide precursors to be synthesized, allocates synthesis chambers or wells in the instrument, and controls the synthetic steps and cleavage of the finished oligonucleotide. The number of reaction vessel in such a system may vary widely; in one embodiment, a plurality of such reaction vessels may be in the range of from 2 to 256, or from 2 to 128; or from 2 to 32. Then under control of the same system, finished oligonucleotide precursors are transferred, either robotically or via dedicated fluidics, to appropriate vessels for ligation reactions. In one aspect, such reactions can be carried out in one or more microfluidic devices operating in tandem. Exemplary DNA synthesizers that may synthesize many tens to hundreds or oligonucleotides, or more, are disclosed in the following references which are incorporated by reference: Evans, U.S. Pat. No. 6,670,127; Brennan, U.S. Pat. No. 5,529,756; Livesay et al, Genome Research, 12: 1950-1960 (2002); Lashkari et al, Proc. Natl. Acad. Sci., 92: 7912-7915 (1995); Rayner et al, Genome Research, 8: 741-747 (1998); Cheng et al, Nucleic Acids Research, 30: e93 (2002); Zhou et al, Nucleic Acids Research, 32: 5409-5417 (2004); and the like. Such synthesizers provide a source of oligonucleotide precursors in one embodiment of the system of the invention.

In accordance with the invention, in a system or the invention designed for PCR assembly of palindromeless subunits into a target polynucleotide, hierarchies of reaction vessels may be employed corresponding to a hierarchical assembly of increasingly larger fragments. In one embodiment, such system of the invention has at least two groups of reaction vessels: a first set of reaction vessels for assembling palindromeless subunits, and at least one second reaction vessel for conducting a PCR with the subunits from the first set of reaction vessels.

Ligation Reactions

Oligonucleotides are preferably annealed for assembly in aqueous media which promotes Watson/Crick base-pairing, at or near room temperature. Exemplary annealing conditions are a temperature range of 30-65° C. and an assembly solvent of 0.2-1.0 M NaCl or KCl, 10-50 mM $MgCl_2$, 100 mM Tris-HCl and 0-50% formamide, at pH=7-9 (Berger, 1987, p. 549). For example, 1 mg of support, (1 nmole, loaded at 1 µmole oligonucleotide/gm) is annealed with 5 nmole of each oligonucleotide during each annealing and ligation cycle, in a total volume of 10-50 µl solution.

In a ligation reaction, a ligation reagent effects ligation of a ligatable nick site located between two assembled oligonucleotides, that is, two oligonucleotides annealed to a complementary template strand. DNA ligase conducts enzymatic ligation upon a ligatable nick site to create an internucleotide phosphodiester bond and create a continuous strand in the ligation product. Ligation with DNA ligase is highly specific and generally occurs only with perfect complementarity between a template strand and the oligonucleotides close to the nick site. With ATP or $NAD^+$, DNA ligase catalyzes in a template-driven reaction the formation of a phosphodiester bond between the 5' phosphoryl terminus and the 3'-hydroxyl terminus of two abutting oligonucleotides on a temple. Under such reaction conditions, without the presence of the terminal 5' phosphoryl group, the abutting oligonucleotides form a non-ligatable nick and no phosphodiester bond is formed. As described more fully below, non-phosphorylated oligonucleotides may be employed in methods of the invention where the ligation reaction includes a kinase as well as a ligase in the reaction.

In a preferred embodiment of the invention, the 5' phosphate groups of assembled oligonucleotide precursors are ligated to the 3' hydroxyl of an adjacent oligonucleotide precursor. Enzymatic ligation of the assembled polynucleotide on solid-support can be conducted by treating the assembled polynucleotide on solid-support, for example, with 20 mM dithiothreitol, 10 mM $MgCl_2$, 1 mM ATP, and 50 mM Tris-HCl, followed by the addition of T4 DNA ligase, or other forms of ligase. For example, 1 nmole of assembled polynucleotide would undergo ligation with 1 unit of ligase in a total volume of 10-50 µl solution. After several minutes to several hours at 37° C. with gentle agitation, the support is then filtered, centrifuged, or aspirated to remove excess liquid reagents, and washed with neutral aqueous buffer, such as several ml of 0.1 M triethylammonium acetate, pH 7.

In another preferred embodiment, non-5'-phosphorylated oligonucleotides are used to assemble subunits in a reaction comprising both a ligase and a kinase, so that 5'-phosphorylation and ligation take place in the same reaction mixture. This saves considerable expense by eliminating the added cost of synthetically phosphorylating the oligonucleotide precursors prior to reaction. Exemplary reaction conditions include the following: 10 uM each oligonucleotide (non-5'-phosphorylated), 1×T4 Ligase Buffer (described below), 0.5 U/uL T4 ligase, 0.5 U/uL T4 polynucleotide kinase, in 20 uL reaction volume, incubated for 1 hour at room temperature.

A ligatable nick site of an assembled polynucleotide can also be chemically ligated with reagents, such as cyanogen bromide and dicyclohexylcarbodiimide, to form an internucleotide phosphate linkage between two adjacent assembled oligonucleotides.

The solid-support may be washed under denaturing conditions after each ligation to remove the non-immobilized strands. Preferred denaturants include sodium hydroxide, ammonium hydroxide, formamide, urea, sodium chloride and sodium acetate.

Example 1

Efficient Solid Phase Ligation of Duplexes

Figure 3A:
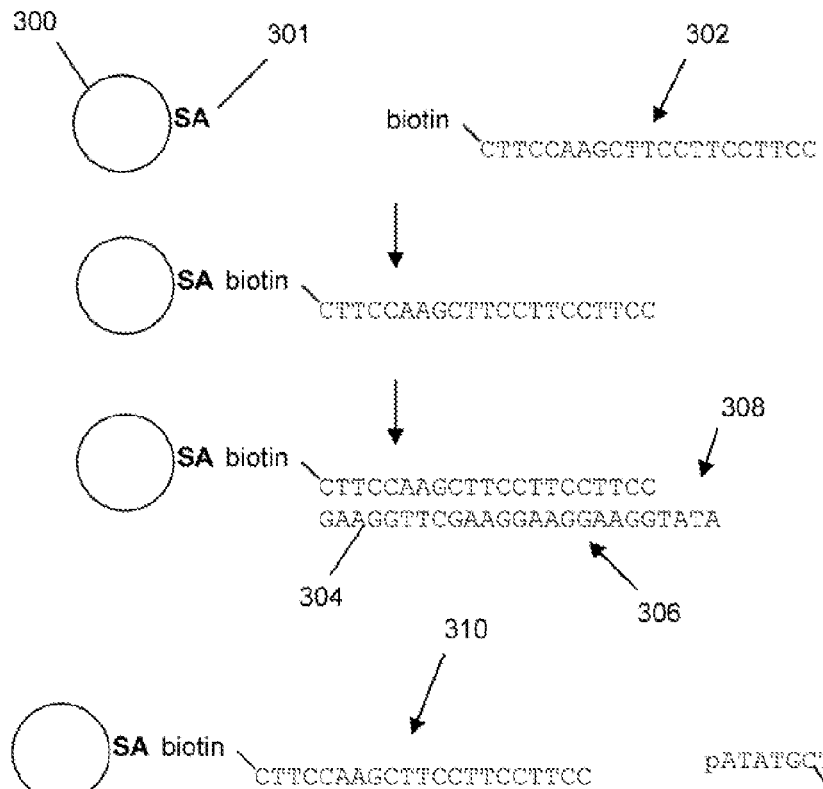
FIGS. 3A-3C diagrammatically illustrate the preferred assembly of oligonucleotide precursors at least as duplexes for efficient enzymatic ligation.

In this example, the ligation efficiency is shown of adding palindromeless subunits to extended duplexes as duplexes made up of at least two oligonucleotide precursors. More particularly, an initializing duplex (306) was prepared by purification of streptavidin coated (301) magnetic beads (300), attachment of a biotinylated top strand (302) to the beads, then annealing of the complementary bottom strand (304) with the appropriate overhang (308), as illustrated with SEQ ID NO 4 in FIG. 3A-3C.

Figure 3B:
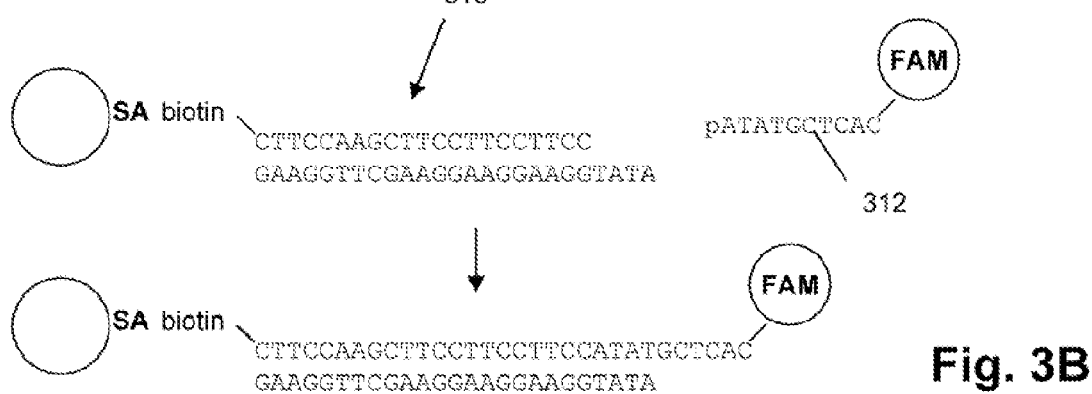

A first set of reactions was carried out as illustrated in FIG. 3B. To a fixed concentration of initiating duplex attached to magnetic beads (310) various concentrations of a fluorescently labeled (FAM) 5' phosphorylated oligonucleotide (312) were combined under the conditions described below to test T4 ligase efficiency. The magnetic beads with initializing duplex were prepared as follows: A total of 300 uL of streptavidin beads (~$1.8*10^8$ beads) (Invitrogen) were washed three times with 300 uL 2×B&W Buffer (10 mM Tris-HCl pH 7.5, 1 mM EDTA, 2.0 M NaCl) with magnetic sequestering for 2 minutes between washes. Attachment of the biotinylated single stranded oligonucleotide was performed at room temperature in 150 uL 2×B&W Buffer, 100 uL H₂O, and 50 uL 20 uM biotinylated DNA according to manufactures instructions. After two washes with 1×B&W Buffer, beads were resuspended with 120 uL dH₂O, 150 uL 10 uM single stranded bottom oligonucleotide, and 30 uL Annealing Buffer (100 mM Tris-HCl pH 7.5, 1 M NaCl, 10 mM EDTA). Annealing was performed in a thermocycler at 80° C. for 5 minutes followed by 30 minutes cooling to room temperature and subsequent cooling to 4° C. on ice. 10 uL of the double stranded product was quantified using a pico green fluorescence assay.

Ligation reaction mixtures contained 0.2 uM initializing duplex, 0.002 to 20 uM 5'-phosphorylated, 3'-FAM oligonucleotide, 2 Weiss units of T4 DNA Ligase, 1.5 uL dH₂O, 2.5 uL 10×T4 DNA Ligase Buffer (500 mM Tris-HCl, 100 mM MgCl₂, 10 mM ATP, 100 mM Dithiothreitol pH 7.5 at 25° C.). These reactions were carried out at 16° C. for 1 hour. Ligase was then deactivated at 65° C. for 10 minutes. Washes with 25 uL TE (10:1) were performed twice to remove excess, unligated labeled oligonucleotide. 20 uL of each reaction was then quantified using as Perkin Elmer Wallac Victor fluorometer and compared to the fluorescence of the labeled oligonucleotide. T4 DNA Ligase showed effective ligation for an overhang of 5 or 6 base pairs but reactions involving 3 or 4 basepair overhangs showed no ligation signal above background. Background was measured using a parallel no-ligase negative control reaction for each assay point.

Figure 3C:
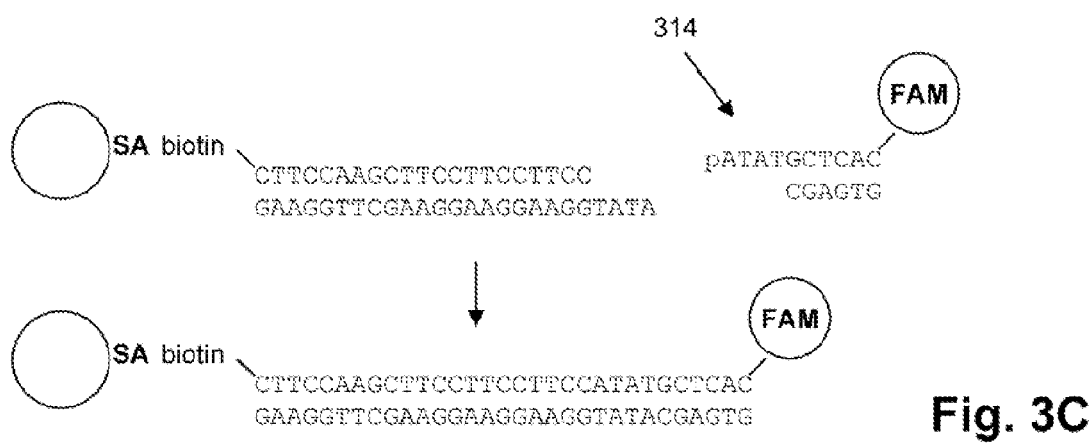

To examine whether ligating duplexes (314) was more efficient, a second set of reactions was carried out, as illustrated in FIG. 3C. Experiments were performed similarly to the ligation efficiency assays above with the addition of either 5 uL TE or 5 uL of 20 uM complementary oligonucleotide. The final reaction mixture contained 0.167 uM initializing duplex, 0.00167 uM to 16.7 uM 5'-phosphorylated, 3'-FAM oligonucleotide, 3.13 uM second oligonucleotide, 2 Weiss units T4 DNA Ligase, 1.0 dH₂O, 3.0 uL 10×T4 DNA Ligase Buffer (500 mM Tris-HCl, 100 mM MgCl₂, 10 mM ATP, 100 mM Dithiothreitol pH 7.5 @ 25° C.). Washes with 30 uL TE (10:1) were performed twice to remove excess, unligated labeled, oligonucleotide, 20 uL of each reaction was then quantified using a Perkin Elmer Wallac Victor fluorometer and compared to the fluorescence of the labeled oligonucleotide. While 3 and 4 basepair overhangs were not ligated when single oligonucleotide precursor were used, these reactions were dramatically improved with the addition of the complementary oligonucleotide which, when annealed, extended the overall length of the initializing duplex to form an extended duplex. The pairwise ligations of oligonucleotide precursors in 1 hr reactions at 16° C. with either 3- or 4-nucleotide overhangs showed complete ligation for reactant concentrations in the range of 1-3.3 uM.

Example 2

Assembly of 128-Basepair Fragment of Human β-Actin Gene with Octomers

In this experiment, a 128 base pair fragment of the human β-actin gene was synthesized by first determining palindromeless subunits and their corresponding subsets of oligonucleotide precursors using the algorithm of FIG. 2B, then assembling the subunits in accordance with the scheme shown in FIG. 1A. The following initializing duplexes containing a BbsI site (underlined) were synthesized and attached to four different solid supports, as described more fully below (SEQ ID NO: 5).

```
Solid Support-TGCA . . . GGAAGACTGNNNNNNNNNNNNNNNN
           ACGT . . . CCTTCTGACNNNNNNNNNNNNNNNN
```

For each of the four different solid supports, the attached duplex was digested with BbsI to give an initializing duplex of the following form, where the overhang on the lower strand was selected to be complementary to that of a corresponding palindromeless subunit.

```
Solid Support-TGCA . . . GGAAGACTG
           ACGT . . . CCTTCTGACNNNN
```

The following palindromeless subunits were prepared. Their component 8-mer oligonucleotide precursors are indicated by alternate underlining:

```
Subunit A (SEQ ID NO: 6);
GTGGGCATGGGTCAGAAGGATTCCTATGTGGG
    CGTACCCAGTCTTCCTAAGGATACACCCGCTG Subunt B (SEQ ID NO: 7):
CGACGAGGCCCAGAGCAAGAGAGGCATCCTCA
    CTCCGGGTCTCGTTCTCTCCGTAGGAGTGGGA Subunit C (SEQ ID NO: 8):
CCCTGAAGTACCCCATCGAGCACGGCATCGTC
    CTTCATGGGGTAGCTCGTGCCGTAGCAGTGGT Subunit D (SEQ ID NO: 9):
ACCAACTGGGACGACATGGAGAAAATCTGGCA
    TGACCCTGCTGTACCTCTTTTAGACCGTGGTG
```

As noted above, the solid-support used to anchor growing intermediate fragments was designed such that digestion with BbsI would release any attached fragment while retaining a 4 bp overhang. Released intermediates could then be used in further ligations according to the scheme illustrated in FIG. 1A. Four distinct bead sets were created each with a unique 4 bp overhang. The overhangs for the solid support adaptors were constructed to be complementary to subunits of the 128 basepair target such that eight octamers, overlapping by four nucleotides would make up a subunit. In the first step, pooled ligation reactions were performed with the solid support and nine octamers. To avoid problematic regions of non-unique complementary ends found in the octamer pools, two of the pooled ligations (subunits C and D) were performed in two steps, avoiding the repeated region. Each of the four products from this process, subunits A, B, C, and D, were expected to be 32 basepairs in length. In the second phase of construction, subunits B and D were detached from their solid support using BbsI and then ligated to the immobilized subunits, A and C, to produce fragments comprising subunits AB and CD. A third digest and ligation reaction, identical to the second, released the fragment CD and ligation with the immobilized AB intermediate produced the final ligation product ABCD. PCR amplification of the final product was then performed directly from the immobilized dsDNA. After gel electrophoretic separation of the PCR product, sequencing of the 170 basepair band verified a single product containing the 42 basepair adaptor and 128 basepair ligation product. Sequencing of the second, smaller band revealed a product missing one of the 32 basepair intermediate subunits.

Reaction conditions for the above experiments were as follows: Preparation of duplexes immobilizing on solid supports. All oligonucleotides, including those 5'-biotinylated and 5'-phosphorylated were synthesized by Integrated DNA Technologies (Coralville, Iowa). Immobilized double stranded DNA preparation involved purification of streptavidin coated magnetic beads, binding of the biotinylated top strand, and then annealing of the complementary bottom strand. M-270 Streptavidin Dynabeads (Invitrogen) were washed three times with equal volume 2×B&W buffer (10 mM Tris-HCl pH 7.5, 1 mM EDTA, 2.0 M NaCl). DNA immobilization was performed by resuspension of the purified bead solution to 1×B&W buffer supplemented with 3.33 µM 5'-biotinylated oligonucleotide. After 20 minutes at room temperature with gentle rotation, two washes with equal volume of 1×B&W were performed to remove unbound oligonucleotide. Immobilized oligonucleotide was then hybridized to form dsDNA by resuspending the bead mixture in 10 mM Tris-HCl (pH 7.5), 0.1 M NaCl, 1 mM EDTA and 5 µM bottom strand oligonucleotide. Bead solutions were heated to 80° C. for 5 minutes and cooled to room temperature. Final solutions were washed twice with equal volume TE 10:1 (pH 7.5) to remove excess bottom strand and quantified using a standard PicoGreen fluorescence assay.

DNA Synthesis With Oligonucleotide Precursors. Pooled ligation reactions consisted of 1.5 µM immobilized dsDNA on beads, 66.7 µM of each octamer, 1×T4 DNA ligase buffer (50 mM Tris-HCl, 10 mM $MgCl_2$, 1 mM ATP, 10 mM Dithiothreitol, pH 7.5 @ 25° C.) and 0.5 units/µL of T4 DNA Ligase. Reactions proceeded for four hours at 4° C. and mixtures were then washed twice with equal volume of TE to remove unligated product and enzyme. In selected bead sets, this process was performed twice using the same conditions but with the octamers split into two groups to avoid a region of repeated sequence. BbsI digestion was performed by resuspending the bead solutions to 25 units BbsI (NEB), 50 mM NaCl, 10 mM Tris-HCl, 10 mM $MgCl_2$, and 1 mM Dithiothreitol (pH 7.9 @ 25° C.). Digestion was performed for three hours at 37° C. followed by enzyme inactivation at 65° C. for 20 minutes. Released DNA fragments were isolated by immediate aspiration from the hot digest mixture while a magnet was applied. The extracted mixture was cooled to 4° C. for 5 minutes and the full volume was used in subsequent ligations. Pairwise ligation steps were performed by resuspending an immobilized bead solution with an adjacent digested fragment solution. Ligation reactions consisted of 1.5 µM immobilized DNA, the released DNA fragment (unknown concentration), 1×T4 DNA ligase buffer (50 mM Tris-HCl, 10 mM $MgCl_2$, 1 mM ATP, 10 mM Dithiothreitol, pH 7.5 @ 25° C.) and 0.5 units/µL of T4 DNA Ligase. Reactions proceeded for four hours at 4° C. and mixtures were then washed twice with equal volume of TE to remove unligated product and enzyme. Digest and ligation steps were repeated as necessary to complete the pair-wise construction process.

DEFINITIONS

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Denaturing" conditions or reagents disrupt base-pairing and cause separation of a duplex into single-strands. Denaturing conditions and reagents include heat, basic pH, high salt concentrations and specific denaturants, such as formamide and ammonium hydroxide. "Non-denaturing" conditions allow base-pairing in duplex structures to persist. Non-denaturing conditions typically include low temperature, neutral pH, low salt concentrations, neutral aqueous buffers, and reagents which do not disrupt hydrogen bonding between nucleobases.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g. conditions including temperature of about 5° C. less that the $T_m$ of a strand of the duplex and low monovalent salt concentration, e.g. less than 0.2 M, or less than 0.1 M. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Hybridization" or "annealing" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" or "annealing conditions" will typically include salt concentrations of less than about 1M, more usually less than about 500 mM and less than about 200 mM. Hybridization or annealing temperatures can be as low as 5° C., but are typically greater than 22° C., more typically greater than about 30° C., and preferably in excess of about 37° C. Hybridization and annealing are usually performed under stringent conditions, i.e. conditions selected to minimize the hybridization or annealing of undesired oligonucleotides, polynucleotides, or probes to a target subsequence. Stringent conditions are sequence-dependent and are different in different circumstances. Longer fragments may require higher hybridization temperatures for specific hybridization. Several factors may affect the stringency of hybridization or annealing, including base composition and length of the complementary strands, presence of organic solvents and extent of base mismatching. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis, "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (199), which are hereby incorporated by reference in its entirety for all purposes above. "Hybridizing specifically to" or "annealing specifically to" or "specifically hybridizing to" or like expressions refer to the binding, duplexing, annealing or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. Ligations are usually carried out enzymatically by a ligase to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213. Chemical ligation methods are well known in the art, e.g. Ferris et al, Nucleosides & Nucleotides, 8: 407-414 (1989); Shabarova et al, Nucleic Acids Research, 19: 4247-4251 (1991); and the like. Preferably, enzymatic ligation is carried out using a ligase in a standard protocol. Many ligases are known, and are suitable for use in the invention, e.g. Lehman, Science, 186: 790-797 (1974); Engler et al, DNA Ligases, pages 3-30 in Boyer, editor, The Enzymes, Vol. 15B (Academic Press, New York, 1982); and the like. Preferred ligases include T4 DNA ligase, T7 DNA ligase, *E. coli* DNA ligase, Taq ligase, Pfu ligase, and Tth ligase. Protocols for their use are well known, e.g. Sambrook et al (cited above); Barany, PCR Methods and Applications, 1: 5-16 (1991); Marsh et al, Strategies, 5: 73-76 (1992); and the like. Generally, ligases require that a 5' phosphate group be present for ligation to the 3' hydroxyl of an abutting strand. Particularly efficient ligation takes place when the terminal phosphate of one oligonucleotide and the terminal hydroxyl group of an adjacent second oligonucleotide are annealed together across from their complementary sequences within a double helix, i.e. where the ligation process ligates a "nick" at a ligatable nick site and creates a complementary duplex.

"Linker" refers to one or more atoms connecting an oligonucleotide to a solid-support, label, or other moiety.

"Microfluidics device" means an integrated system of one or more chambers, ports, and channels that are interconnected and in fluid communication and designed for carrying out a reaction or process with very little reagent or sample usage, either alone or in cooperation with an appliance or instrument that provides support functions, such as sample introduction, fluid and/or reagent driving means, temperature control, detection systems, data collection and/or integration systems, and the like. Microfluidics may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Mather et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Overhang" refers to a single-stranded terminus of a duplex of base-paired oligonucleotides. The overhang may be one or more bases in length and allows for annealing of a complementary oligonucleotide prior to ligation.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic add, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. Reaction volumes typically range from a few hundred nanoliters, e.g. 200 nL, to a few hundred µL, e.g. 200 µL. "Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of flow 14 to 36 nucleotides.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Solid-support" refers to a material in the solid phase that interacts with reagents in the liquid phase by heterogeneous reactions. Solid supports can be derivatized with oligonucleotides by covalent or non-covalent bonding through one or more attachment sites, thereby "immobilizing" an oligonucleotide to the solid-support.

What is claimed is:

1. A method of synthesizing a polynucleotide on a solid support from a set of oligonucleotide precursors, the method comprising the steps of:
   repeatedly partitioning a polynucleotide into candidate subunits and for each candidate subunit generating tilings of oligonucleotide precursors that cover the candidate subunit, the oligonucleotide precursors being selected from a set containing every sequence of a predetermined length;
   selecting a partition wherein each candidate subunit has a tiling of oligonucleotide precursors each free of palindromic sequences and comprises a subset of oligonucleotide precursors capable of annealing together to form a unique duplex, thereby producing an ordered set of palindromeless subunits; and
   successively ligating the subsets of oligonucleotide precursors of the palindromeless subunits to an initializing duplex with a complementary end in a single reaction to form a unique duplex, the initializing duplex being attached to a solid support, and each subset being ligated in an order corresponding to the ordered set of palindromeless subunits to form the polynucleotide.

2. The method of claim 1 wherein said polynucleotide is releasably attached to said initializing duplex, so that after said polynucleotide is formed, it may be released and separated from said solid support.

3. The method of claim 2 wherein said polynucleotide is released from said solid support by enzymatic cleavage.

4. The method of claim 2 wherein each of said oligonucleotide precursors has a length in the range of from 4 to 14 nucleotides and each of said subsets of oligonucleotide precursors has a size in the range of from 2 to 128 oligonucleotides.

5. The method of claim 1 wherein each palindromeless subunit of said plurality is synthesized on a separate said solid support by ligating said subset of oligonucleotide precursors to said complementary end of said initializing duplex attached thereto.

6. The method of claim 5 wherein said palindromeless subunit is releasably attached to said initializing duplex, so that after said palindromeless subunit is formed such subunit may be released and separated from said solid support.

7. A method of synthesizing a polynucleotide from a set of oligonucleotide precursors, the method comprising the steps of:
   repeatedly partitioning a polynucleotide into candidate subunits and for each candidate subunit generating tilings of oligonucleotide precursors that cover the candidate subunit, the oligonucleotide precursors being selected from a set containing every sequence of a predetermined length;
   selecting a partition wherein each candidate subunit has a tiling of oligonucleotide precursors each free of palindromic sequences and comprises a subset of oligonucleotide precursors capable of annealing together to form a unique duplex, thereby producing an ordered set of palindromeless subunits, wherein each palindromeless subunit overlaps adjacent palindromeless subunits of the ordered set and the ordered set includes terminal subunits each having a primer binding site releasably attached thereto;
   synthesizing each palindromeless subunit of the ordered set on a separate solid support by ligating a subset of oligonucleotide precursors to a complementary end of an initializing duplex attached the solid support in a single reaction to form a unique duplex; and
   combining in a polymerase chain reaction the palindromeless subunits from the solid supports and primers specific for the primer binding sites of the terminal subunits so that the palindromeless subunits and primers undergo successive cycles of denaturation and polymerase extension until the polynucleotide is formed.

8. The method of claim 7 wherein each of said palindromeless subunits is releasably attached to said initializing duplex, so that after said palindromeless subunit is formed such subunit may be released and separated from said solid support.

9. The method of claim 7 wherein each of said palindromeless subunit overlaps its adjacent palindromeless subunit in said ordered set so that stable duplexes are capable of forming for said polymerase extension in said polymerase chain reaction.

10. A method of synthesizing a polynucleotide from a set of oligonucleotide precursors, the method comprising the steps of:
   (a) repeatedly partitioning a polynucleotide into candidate subunits and for each candidate subunit generating tilings of oligonucleotide precursors that cover the candidate subunit, the oligonucleotide precursors being selected from a set containing every sequence of a predetermined length;
   (b) selecting a partition wherein each candidate subunit has a tiling of oligonucleotide precursors each free of palindromic sequences and comprises a subset of oligonucleotide precursors capable of annealing together to form a unique duplex, thereby producing an ordered set of palindromeless subunits;
   (c) ligating the oligonucleotide precursors of each subset to an initializing duplex with a complementary end in a single reaction to form a unique duplex comprising a palindromeless subunit that is releasably attached to a solid support;
   (d) repeating step (c) until the ordered set of palindromeless subunits is synthesized; and
   (e) ligating the ordered set of palindromeless subunits together to form the polynucleotide.

11. The method of claim 10 further including the step of releasing said palindromeless subunit from said solid support after said step of ligating; and wherein said step (c) of repeating, further includes a step of releasing said palindromeless subunit until said ordered set of palindromeless subunits is synthesized.

12. The method of claim 10 wherein said step of ligating said ordered set of palindromeless subunits includes ligating pairwise said palindromeless subunits to form intermediate ligation products and successively ligating pairwise intermediate ligation products and successive ligation products thereof until said polynucleotide is synthesized.

13. The method of claim 12 wherein said palindromeless subunits are synthesized on separate said solid supports and wherein said intermediate ligation products are formed by ligation of said palindromeless subunits or by ligation of previously synthesized intermediate ligation products.

14. The method of claim 13 wherein said palindromeless subunits are released from said solid support by enzymatic digestion of said initializing duplex.

15. A system for synthesizing a polynucleotide from a set of oligonucleotide precursors, the system comprising:
   a source of oligonucleotide precursors, the source capable of providing a set of oligonucleotide precursors of every sequence of a predetermined length;
   an ordered set of palindromeless subunits with respect to the set of oligonucleotide precursors, the ordered set of palindromeless subunits covering the polynucleotide, each palindromeless subunit overlapping adjacent palindromeless subunits of the ordered set, the ordered set including terminal subunits each having a primer binding site releasably attached thereto, and each palindromeless subunit comprising a subset of oligonucleotide precursors capable of annealing together to form a unique duplex;

wherein the ordered set of palindromeless subunits is generated by repeatedly partitioning the polynucleotide into candidate subunits and for each candidate subunit generating tilings of oligonucleotide precursors which cover the candidate subunit until a tiling of each candidate subunit is obtained, that comprises a subset of oligonucleotide precursors without palindromic sequences;

a plurality of reaction vessels for synthesizing each palindromeless subunit of the ordered set on a separate solid support by ligating a subset of oligonucleotide precursors to a complementary end of an initializing duplex attached the solid support in a single reaction; and a second reaction vessel for combining in a polymerase chain reaction the palindromeless subunits from the solid supports and primers specific for the primer binding sites of the terminal subunits so that the palindromeless subunits and primers undergo successive cycles of denaturation and polymerase extension until the polynucleotide is formed.

16. The system of claim 15 wherein said source of oligonucleotide precursors is a bank of reservoirs in fluid communication with said plurality of reaction vessels, each reservoir in the bank containing a different oligonucleotide precursor.

17. The system of claim 15 wherein said source of oligonucleotide precursors is a synthesis station under control of a control system operationally associated with said plurality of reaction vessels, such that the control system directs the parallel synthesis in the synthesis station of each of said oligonucleotide precursors of each of said subsets for each of said palindromeless subunits and successively delivers such oligonucleotide precursors to each of said reaction vessels of said plurality.

18. The system of claim 17 wherein said control system, after assembly of said palindromeless subunits in said plurality of reaction vessels, directs the delivery of said palindromeless subunits to said second reaction vessel and conducts said polymerase chain reaction.

* * * * *